(12) United States Patent
Hu et al.

(10) Patent No.: US 11,861,475 B2
(45) Date of Patent: Jan. 2, 2024

(54) METHODS FOR USING MACHINE LEARNING AND MECHANISTIC MODELS FOR BIOLOGICAL FEATURE MAPPING WITH MULTIPARAMETRIC MRI

(71) Applicants: Mayo Foundation for Medical Education and Research, Rochester, MN (US); Arizona Board of Regents on behalf of Arizona State University, Scottsdale, AZ (US)

(72) Inventors: Leland S. Hu, Phoenix, AZ (US); Jing Li, Tempe, AZ (US); Kristin R. Swanson, Phoenix, AZ (US); Teresa Wu, Gilbert, AZ (US); Nathan Gaw, Tempe, AZ (US); Hyunsoo Yoon, Tempe, AZ (US); Andrea Hawkins-Daarud, Houston, TX (US)

(73) Assignees: Mayo Foundation for Medical Education and Research, Rochester, MN (US); Arizona Board of Regents on behalf of Arizona State University, Scottsdale, AZ (US)

( * ) Notice: Subject to any disclaimer, the term of this patent is extended or adjusted under 35 U.S.C. 154(b) by 206 days.

(21) Appl. No.: 16/764,837

(22) PCT Filed: Nov. 19, 2018

(86) PCT No.: PCT/US2018/061887
§ 371 (c)(1),
(2) Date: May 15, 2020

(87) PCT Pub. No.: WO2019/100032
PCT Pub. Date: May 23, 2019

(65) Prior Publication Data
US 2020/0342359 A1 Oct. 29, 2020

Related U.S. Application Data

(60) Provisional application No. 62/684,096, filed on Jun. 12, 2018, provisional application No. 62/588,096, filed on Nov. 17, 2017.

(51) Int. Cl.
*G06K 9/00* (2022.01)
*G06N 20/10* (2019.01)
(Continued)

(52) U.S. Cl.
CPC .......... *G06N 20/10* (2019.01); *G06F 18/2155* (2023.01); *G06T 7/0012* (2013.01);
(Continued)

(58) Field of Classification Search
CPC .......... G01N 2800/7028; C12Q 1/6886; G06T 2207/30096; G06T 7/0012–0016;
(Continued)

(56) References Cited

U.S. PATENT DOCUMENTS 8,571,844 B2 10/2013 Swanson
10,045,728 B2 8/2018 W/u
(Continued)

FOREIGN PATENT DOCUMENTS

WO 2016138041 A9 9/2016

OTHER PUBLICATIONS

Swanson R. Kristin et al: "NIMG-74. Radiomics of Tumor Invasion 2.0: Combining Mechanistic Tumor Invasion Models With Machine Learning Models to Accurately Predict Tumor Invasion in Human Glioblastoma Patients", Neuro-Oncology Nov. 2017 vol. 19 Suppl. 6, Nov. 6, 2017 (Nov. 6, 2017), XP55824552 (Year: 2017).*
(Continued)

*Primary Examiner* — Atiba O Fitzpatrick
(74) *Attorney, Agent, or Firm* — Quarles & Brady LLP

(57) ABSTRACT

Described here are systems and methods for generating and implementing a hybrid machine learning and mechanistic
(Continued)

model to produce biological feature maps, or other measurements of biological features, based on an input of multiparametric magnetic resonance or other images. The hybrid model can include a combination of a machine learning model and a mechanistic model that takes as an input multiparametric MRI, or other imaging, data to generate biological feature maps (e.g., tumor cell density maps), or other measures or predictions of biological features (e.g., tumor cell density). The hybrid models have capabilities of learning individual-specific relationships between imaging features and biological features.

12 Claims, 6 Drawing Sheets

(51) Int. Cl.
  *G16H 50/20* (2018.01)
  *G16H 30/40* (2018.01)
  *G06T 7/00* (2017.01)
  *G06F 18/214* (2023.01)

(52) U.S. Cl.
  CPC ............ *G16H 30/40* (2018.01); *G16H 50/20* (2018.01); *G06T 2207/10088* (2013.01); *G06T 2207/20081* (2013.01); *G06T 2207/30096* (2013.01)

(58) Field of Classification Search
  CPC .................... G06T 2207/30004–30104; G06T 2207/20081; G06T 2207/20084; G06T 2207/10088–10096; G16H 30/40; G16H 50/20; G16H 50/00–50; G06V 2201/03; G06V 10/70; G06V 10/82; G06V 10/774–7796; A61B 5/7264; A61B 5/7267; A61B 5/055; G16B 40/00; G06K 9/6256; G06K 9/6257; G06K 9/6259; G06N 3/02–126; G06N 3/08; G06N 20/20; G06N 3/082; G06N 3/088; G06N 3/0454; G06N 7/04; G06N 3/0427; G06F 17/10

See application file for complete search history.

(56) References Cited

U.S. PATENT DOCUMENTS

| | | | |
|---|---|---|---|
| 10,909,675 | B2 | 2/2021 | Hu |
| 2014/0071125 | A1 | 3/2014 | Burlina |
| 2016/0106321 | A1 | 4/2016 | Sharma et al. |
| 2017/0357844 | A1* | 12/2017 | Comaniciu ............ G16B 40/00 |
| 2019/0087954 | A1* | 3/2019 | Lloyd .................. G06V 20/698 |
| 2020/0410683 | A1 | 12/2020 | Hu |

OTHER PUBLICATIONS

Orla M. Doyle, Krasimira Tsaneva-Atansaova, James Harte, Paul A. Tiffin, Peter Tino, and Vanessa Diaz-Zuccarini, "Bridging Paradigms: Hybrid Mechanistic-Discriminative Predictive Models", IEEE Transactions on Biomedical Engineering, vol. 60, No. 3, Mar. 2013, pp. 735-742 (Year: 2013).*

Baldock AL, et al. From Patient-Specific Mathematical Neuro-Oncology Towards Precision Medicine. Frontiers in Molecular and Cellular Oncology. 2013:3(62).

Baldock AL, et al. Invasion and proliferation kinetics in enhancing gliomas predict IDH1 mutation status. Neuro Oncol. 2014;16(6):779-86.

Baldock AL, et al. Patient-specific Metrics of Invasiveness Reveal Significant Prognostic Benefit of Resection in a Predictable Subset of Gliomas. PLoS One. 2014;9(10).

Barajas Jr, et al. "Regional variation in histopathologic features of tumor specimens from treatment-naive glioblastoma correlates with anatomic and physiologic MR Imaging." Neuro-oncology 14.7 (2012): 942-954.

Belkin M, et al. Manifold regularization: A geometric framework for learning from labeled and unlabeled examples. Journal of machine learning research. 2006;7:2399-434.

Brocks D, et al. Intratumor DNA methylation heterogeneity reflects clonal evolution in aggressive prostate cancer. Cell reports. 2014;8(3):798-806.

Chang, P. D., et al. "A multiparametric model for mapping cellularity in glioblastoma using radiographically localized biopsies." American Journal of Neuroradiology 38.5 (2017): 890-898.

Corwin D, et al. Toward patient-specific, biologically optimized radiation therapy plans for the treatment of glioblastoma. PLoS One. 2013;8.

Durst CR, et al. Multimodal MR imaging model to predict tumor infiltration in patients with gliomas. Neuroradiology. 2014:56(2):107-15.

Ellingson, B. M., et al. "Validation of functional diffusion maps (fDMs) as a biomarker for human glioma cellularity." Journal of Magnetic Resonance Imaging: An Official Journal of the International Society for Magnetic Resonance in Medicine 31.3 (2010): 538-548.

Ester M, et al. A density-based algorithm for discovering clusters in large spatial databases with noise. Kdd. 1996.

Fujino A, et al. A hybrid generative/discriminative approach to semi-supervised classifier design. AAAI. 2005.

Harpold, H.L., et al., 2007. "The Evolution of Mathematical Modeling of Glioma Proliferation and Invasion." Journal of Neuropathology & Experimental Neurology, 66(1), 1-9.

Holub A, et al. Exploiting unlabelled data for hybrid object classification. Neural Information Processing Systems, Workshop Inter-Class Transfer. 2005.

Hu LS, et al. 2017, "Radiogenomics to Characterize Regional Genetic Heterogeneity in Glioblastoma." Neuro-Oncology, 19(1), 128-137.

Hu LS, et al. Multi-parametric MRI and texture analysis to visualize spatial histologic heterogeneity and tumor extent in glioblastoma. PLoS One. 2015;10(11).

Hu LS, et al. Reevaluating the imaging definition of tumor progression: perfusion MRI quantifies recurrent glioblastoma tumor fraction, pseudoprogression, and radiation necrosis to predict survival. Neuro-oncology. 2012; 14(7):919-30.

Huang, S, et al. "A transfer learning approach for network modeling." IIE transactions 44.11 (2012): 915-931.

Inda M, et al. Glioblastoma multiforme: a look inside its heterogeneous nature. Cancers. 2014;6(1):226-39.

International Searching Authority, International Search Report and Written Opinion for application PCT/US2018/061887, dated May 23, 2019.

Jackson P, et al. Patient-specific Mathematical Neuro-Oncology: Using a Simple Proliferation and Invasion Tumor Model to Inform Clinical Practice. Bulletin of Mathematical Biology. Mar. 21, 2015;77(5):846-56.

Kickingereder, P., et al. "Radiogenomics of glioblastoma: machine learning-based classification of molecular characteristics by using multiparametric and multiregional MR imaging features." Radiology 281.3 (2016): 907-918.

Laviolette, P. S., et al. "Precise ex vivo histological validation of heightened cellularity and diffusion-restricted necrosis in regions of dark apparent diffusion coefficient in 7 cases of high-grade glioma." Neuro-oncology 16.12 (2014): 1599-1606.

Lawrence ND et al. Semi-supervised learning via Gaussian processes. Advances in neural information processing systems. 2005.

Li Y, et al. A self-training semi-supervised SVM algorithm and its application in an EEG-based brain computer interface speller system. Pattern Recog Lett. 2008;29(9):1285-94.

Lowekamp BC, et al. The design of SimpleITK. Frontiers in neuroinformatics. Dec. 30, 2013;7:45.

Martelotto LG, et al. Breast cancer intra-tumor heterogeneity. Breast Cancer Research. 2014;16(3):210.

(56) References Cited

OTHER PUBLICATIONS

Mclendon R, et al. Comprehensive genomic characterization defines human glioblastoma genes and core pathways. Nature. 2008;455(7216):1061-8.

Mitchell JR, et al. MR multispectral analysis of multiple sclerosis lesions. Journal of Magnetic Resonance Imaging. May 1, 1997;7(3):499-511.

Neal ML, et al. Discriminating Survival Outcomes in Patients with Glioblastoma Using a Simulation-Based, Patient-Specific Response Metric. PLoS One. 2013;8.

Neal ML, et al. Response classification based on a minimal model of glioblastoma growth is prognostic for clinical outcomes and distinguishes progression from pseudoprogression. Cancer Res. 2013;73(10):2976-86.

Price, S. J., et al. "Improved delineation of glioma margins and regions of infiltration with the use of diffusion tensor imaging: an image-guided biopsy study." American journal of neuroradiology 27.9 (2006): 1969-1974.

Robnik-Sikonja M et al. Theoretical and empirical analysis of ReliefF and RReliefF. Mach Learning. 2003;53(1-2):23-69.

Rockne R, et al. Predicting the efficacy of radiotherapy in individual glioblastoma patients in vivo: a mathematical modeling approach. Phys Med Biol. 2010;55:3271-85.

Sadeghi, N, et al. "Apparent diffusion coefficient and cerebral blood volume in brain gliomas: relation to tumor cell density and tumor microvessel density based on stereotactic biopsies." American journal of neuroradiology 29.3 (2008): 476-482.

Scholkopf B, et al. A generalized representer theorem. Computational learning theory. 2001;416-426.

Sodt R, et al. Quantifying the role of antisotropic invasion in human glioblastoma. New York: Springer. 2010.

Sottoriva A, et al. Intratumor heterogeneity in human glioblastoma reflects cancer evolutionary dynamics. Proc Natl Acad Sci U S A. 2013;110(10):4009-14.

Stadlbauer, A., et al. "Gliomas: histopathologic evaluation of changes in directionality and magnitude of water diffusion at diffusion-tensor MR imaging." Radiology 240.3 (2006): 803-810.

Stupp R, et al. Radiotherapy plus concomitant and adjuvant temozolomide for glioblastoma. New England Journal of Medicine. 2005,352(10):987-86.

Swanson KR, et al. A quantitative model for differential motility of gliomas in grey and white matter. Cell Prolif. 2000;33(5):317-29.

Swanson KR, et al. Virtual and real brain tumors: using mathematical modeling to quantify glioma growth and invasion. J Neurol Sci. 2003;216(1):1-10.

Swanson KR, et al. Virtual brain tumours (gliomas) enhance the reality of medical imaging and highlight inadequacies of current therapy. Br J Cancer. 2002;86(1):14-8.

Tanha J, et al. Semi-supervised self-training for decision tree classifiers. International Journal of Machine Learning and Cybernetics. 2017;8(1):355-70.

Tustison NJ, et al. N4ITK: improved N3 bias correction. IEEE transactions on medical imaging. Jun. 2010;29(6):1310-20.

Wan X. Co-training for cross-lingual sentiment classification. Proceedings of the Joint Conference of the 47th Annual Meeting of the ACL and the 4th International Joint Conference on Natural Language Processing of the AFNLP. 2009.

Wang CH, et al. Prognostic significance of growth kinetics in newly diagnosed glioblastomas revealed by combining serial imaging with a novel biomathematical model. Cancer Res. 2009,69(23):9133-40.

Zhou D, et al. Learning with local and global consistency. Advances in neural information processing systems. 2004.

Zhou ZH, et al. Semi-supervised learning with very few labeled training examples. AAAI. 2007.

Zhu X, et al. Harmonic mixtures: combining mixture models and graph-based methods for inductive and scalable semi-supervised learning. Proceedings of the 22nd international conference on Machine learning: ACM. 2005.

Zhu X, et al. Semi-supervised learning using gaussian fields and harmonic functions. Proceedings of the 20th International conference on Machine learning (ICML). 2003.

Zou, N., et al. "A transfer learning approach for predictive modeling of degenerate biological systems." Technometrics 57.3 (2015): 362-373.

* cited by examiner ive nature of biopsies, one would want to map out the tumor cell density distribution across the clinical imaging (magnetic resonance imaging, MRI) such that biopsy samples can be prioritized. Such a

METHODS FOR USING MACHINE LEARNING AND MECHANISTIC MODELS FOR BIOLOGICAL FEATURE MAPPING WITH MULTIPARAMETRIC MRI

CROSS-REFERENCE TO RELATED APPLICATIONS

This application is a 371 U.S. National Phase application of PCT/US2018/061887, filed Nov. 19, 2018, which claims the benefit of U.S. Provisional Patent Application Ser. No. 62/588,096, filed on Nov. 17, 2017, and entitled "Methods for Generating Patient-Specific Models of Tumor Heterogeneity and Extent from Magnetic Resonance Images Using Transfer Learning," and U.S. Provisional Patent Application Ser. No. 62/684,096, filed on Jun. 12, 2018, and entitled "Methods for Using Machine Learning and Mechanistic Models for Cell Density Mapping of Glioblastoma with Multiparametric MRI," which is herein incorporated by reference in its entirety.

STATEMENT REGARDING FEDERALLY SPONSORED RESEARCH

This invention was made with government support under NS082609 awarded by the National Institutes of Health. The government has certain rights in the invention.

BACKGROUND

Glioblastoma (GBM) ranks among the most lethal of all human cancers. The median survival in the general patient population with first-line treatment is 14 months, with a 26% 2-year survival rate. Poor survival and treatment failure can largely be attributed to tumor invasion and intratumoral heterogeneity. Intratumoral heterogeneity manifests as the spatial heterogeneity in tumor cell density in and around the tumor regions visible on clinical imaging as well as the different molecular signatures of tumor cells within different regions of the same tumor. As a result, different sub-regions of a tumor may have different therapeutic sensitivities, leading to treatment failure and poor survival. As much as Precision Medicine (PM) is revolutionizing medicine, the success of PM hinges on the ability to address such heterogeneity within and between patients.

While glioblastomas are primarily monitored via contrast enhanced ("CE") and T2-weighted magnetic resonance imaging ("MRI"), these modalities are known to be non-specific in their correlation with tumor cell density. This makes it difficult to define the specific regions of interest to target in surgery and radiation.

Machine learning and mechanistic models have been independently utilized to better interpret these images. While these efforts show promise, more accurate results are still desired.

In general, different modeling approaches can impact how predictive models account for inter-subject variability. For instance, a single generalized model applied uniformly across all patients within a cohort—a "one model fits all" approach—would fail to adjust for variabilities in MRI-histologic relationships that may exist from patient to patient. In contrast, individual models developed for each patient using only that patient's MRI and histologic data—a "one model per patient approach"—would fail to benefit from generalized patterns that may be observed across many patients and would also suffer from much too small a sample size compared to multi-patient cohort analysis.

To capture intratumoral heterogeneity, a critical first step is to obtain tumor-rich biospecimens for molecular analysis or genetic profiling, which has been a challenging task in the current clinical practice. For example, in the NIH-funded large-scale cancer genomics project, the Cancer Genome Atlas (TCGA), only 35% of the initially submitted biopsy samples contained adequate tumor content to make genetic analysis possible. Due to the invasive nature of biopsies, one would want to map out the tumor cell density distribution across the clinical imaging (magnetic resonance imaging, MRI) such that biopsy samples can be prioritized. Such a tumor cell density map would offer two additional important clinical benefits: it will assist with enhancing precision of surgical resection and optimizing the dose distribution of radiotherapy.

SUMMARY OF THE DISCLOSURE

The present disclosure addresses the aforementioned challenges by providing methods for combining artificial intelligence (e.g., machine learning) and mechanistic models to improve accuracy of the combined predictions of the resultant hybrid model. This approach balances the advantages of machine learning by integrating diverse sources of data with underlying knowledge provided by mechanistic models. In one configuration of the present disclosure, a method is provided for using machine learning and mechanistic models for cell density mapping in medical imaging, such as when imaging brain cancer, glioblastomas, and the like, using multiparametric MRI.

In one configuration of the present disclosure, a method is provided for biological feature mapping of a region of interest (ROI) of a subject with magnetic resonance imaging (MRI). The method includes selecting at least one region of an image of the subject, generating multiparametric MR data of the subject corresponding to the at least one region of an image and inputting this data to a hybrid model. The hybrid model includes training a machine learning model, generating a mechanistic model, and creating a biological feature map based upon the machine learning model and the mechanistic model. Finally, the biological feature map is displayed for the region of interest based upon the hybrid model.

In one configuration, a method is provided for generating population density maps using a hybrid machine learning and mechanistic model. The method includes: a) accessing training data including labeled data and unlabeled data, wherein the labeled data includes image-localized sampled datapoints and the unlabeled data includes multiparametric images and/or 2D/3D datasets; b) training a machine learning model on the training data, generating output as a trained machine learning model; c) inputting the training data to a mechanistic model, generating output as population density data; d) training the hybrid machine learning and mechanistic model on the training data and the mechanistic model-based population density data, generating output as a trained hybrid model comprising a predictive function that relates localized image and/or 2D/3D dataset features and population density; and e) inputting multiparametric images and/or 2D/3D datasets to the trained hybrid model, generating output as one or more population density maps that depict a spatial distribution of a density of items predicted based on localized image and/or 2D/3D dataset features in the multiparametric images and/or 2D/3D datasets.

In some configurations, the method may include training the hybrid machine learning model by regularizing the trained hybrid model using the multiparametric images and/or 2D/3D datasets in the training data and the mechanistic model-based population density data to a Laplacian matrix. The method may also include where the trained hybrid model is regularized using a Laplacian matrix that is generated by converting the multiparametric images and/or 2D/3D datasets in the training data and the PI-based population density data.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
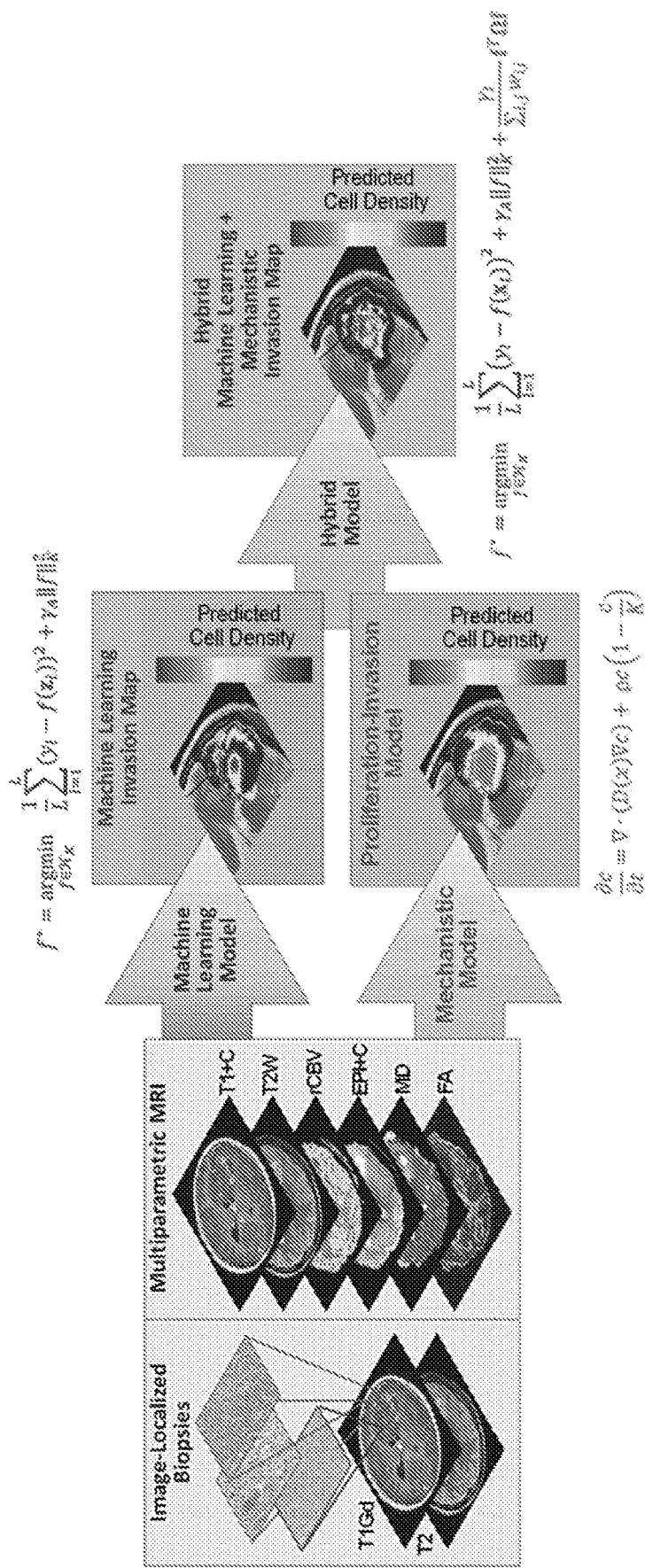
FIG. 1 show a workflow diagram of an example implementation for generating a hybrid machine learning and mechanistic model in accordance with some embodiments described in the present disclosure.

Described here are systems and methods for generating and implementing a hybrid machine learning model and mechanistic model to produce biological feature maps (e.g., cell density maps) or other measurements, predictions, or estimates of biological features (e.g., cell density) based on an input of data that are spatially varying, temporally varying, or both. As one example, the input data may include multiparametric magnetic resonance images. In one configuration of the present disclosure, the hybrid model includes a combination of a machine learning model (ML) and a proliferation-invasion (PI) mechanistic model that takes as an input multiparametric MRI data and mechanistics of tumor cell proliferation invasion to generate tumor cell density prediction under a graph-based semi-supervised learning (SSL) framework.

The hybrid machine learning and mechanistic models described in the present disclosure have capabilities of learning patient-specific relationships between imaging features and cell density, and have a greater prediction accuracy than machine learning or proliferation-invasion alone, especially when applied to a GBM patient cohort. Additionally, the hybrid machine learning and mechanistic models described in the present disclosure provide a more balanced prediction in T2-weighted (T2W) regions-of-interest (ROIs) when compared to proliferation-invasion alone. For instance, PI alone can underestimate cell density, indicating that the hybrid machine learning and mechanistic model is more capable of capturing high density regions in brain around tumor (BAT).

Contributions of each individual feature can be determined using a Relief algorithm that is configured specifically for the hybrid machine learning and mechanistic models described in the present disclosure. It was found in example studies that PI contributed significantly to the prediction, followed by all or a subset of MRI sequences T1+C (e.g., T1-weighted imaging with a contrast agent), fractional anisotropy (FA), T2 (e.g., T2-weighted imaging), and relative cerebral blood volume (rCBV). This highlighted the importance of incorporating mechanistic models to help improve prediction of the biological output (e.g., tumor cell density).

Machine learning models can be trained to link localized imaging features of multiparametric MRI, or other imaging, at each biopsy location with pathologist quantified tumor cell density. This results in a predictive tumor cell density machine learning model map that can be applied over the entire tumor. Since machine learning models are trained on the data provided by image-localized biopsies from different regions of previous patients with tumors, which may be scant data, they are prone to vulnerability with regard to any biases or imbalance in the data feeding the model. Based on the breadth and depth of these training data, the resultant trained machine learning model can be used to predict the cell density of any location, including locations that are not biopsied.

Mechanistic models are built on first principles understanding of biological and/or physiological processes that constrain interpretation as to how the multiparametric MRIs, or other imaging, might provide insights into these biological or physiological processes (e.g., tumor cell density across the brain). One mechanistic model is the Proliferation-Invasion model mentioned above. The PI model is based on the principle that tumors are proliferative and invasive, and thus simulations of the PI model are based on patient-specific estimates of the tumor cell net proliferation and invasion rates. These proliferation and invasion rates can be estimated for each patient using contrast enhanced T1-weighted and T2-weighted MRIs, or other imaging features. Based on the premise underlying the PI model, the PI model can produce a tumor cell density map for anywhere in a patient's brain given outlines of imaging abnormalities on pretreatment images along with gray/white matter segmentation of the patient's brain.

The PI model aims to capture the most basic understanding of what cancer is: cells that grow uncontrollably and invade surrounding tissue. The invasion term is particularly relevant for glioblastomas, which are known to be diffusely invasive with the potential to migrate long distances in the human brain. Mathematically, the PI model can be written as follows:

$$\underset{\frac{\partial c}{\partial t}}{\underbrace{\text{Rate of Change of Cell Density}}} = \underset{\nabla \cdot (D(x)\nabla c)}{\underbrace{\text{Invasion of Cells into Nearby Tissues}}} + \underset{\rho c\left(1 - \frac{c}{K}\right)}{\underbrace{\text{Proliferation of Cells}}}; \quad (1)$$

where c is the tumor cell density; D(x) is the net rate of diffusion, which is taken to be piecewise constant with different values in gray and white matter; ρ is the net rate of proliferation; and K is the cell carrying capacity. This model may be used to predict prognosis, radiation sensitivity, benefit from resection, and mutation status, such as IDH1 mutation status in the case of glioblastoma (GBM). Additionally, this model may be used to create untreated virtual controls for use in defining response metrics that are more prognostically significant. The PI model can also be used to model other biological systems, such as diseases such as Alzheimer's Disease (AD), in which c may indicate the density of a toxic protein, D(x) may indicate the diffusion of that protein and its conversion rate from a normal to a toxic form.

It will be appreciated that mechanistic models other than the proliferation-invasion model described above can also be used to model other biological feature data. As noted, one example biological feature that can be mapped or otherwise measured using the systems and methods described in the present disclosure is cell density. More generally, the biological features can include data that can be mapped, measured, predicted or otherwise estimated using a mechanistic model of one or more biological or physiological processes. These biological feature data may include properties, characteristics, or other features of cells, proteins, macromolecules, biomolecules, or other chemical compounds. The type of biological feature data that are mapped, measured, predicted, or otherwise estimated may therefore be determined based in part on the mechanistic model used to augment the machine learning model.

As one non-limiting example, a mechanistic model such as a Proliferation-Invasion-Hypoxia-Necrosis-Angiogenesis (PIHNA) model can be used. In these instances, the biological feature data may include data indicative of hypoxic cell density. Other mechanistic models can include mathematical models of biochemical reactions, including those that involve metabolism, signal transduction, gene expression, or combinations thereof. As noted, mechanistic models can also include mathematical models of other biological or physiological processes or systems, including mechanistic models related to disease systems, epidemiology, tumor grading, and so on. Other biological feature data may, therefore, include other histological properties or characteristics (e.g., cell shape, cell size, cell area, genomic characterization, molecular status).

Examples of other mechanistic models may include models of complex disease systems that are modeled in terms of spatial heterogeneity of molecular characteristics and temporal dynamics, which can help elucidate the biological underpinning of disease formation, progression, and treatment resistance. Such models can find applicability in neurological diseases and cancer, and more generally in biology, ecology, and epidemiology.

As one non-limiting example, the mechanistic model may be a mechanistic model of the gut microbiome, which can be characterized by spatial heterogeneity and temporal dynamics. Global imaging of the gut combined with localized biopsies can be used to give insight into imaging features driven by particular bacteria colonies. By understanding how specific individual clonal populations interact and grow, the creation of spatial-temporal biological feature maps using the systems and methods described in the present disclosure may allow for better prediction of how large-scale shifts in sub-populations may alter coexistence or lead to a dominant clone.

Machine learning is a data-driven approach, which has the strength of utilizing the available data, but a model built on a particular dataset may not generalize well to other datasets. For instance, machine learning models for tumor cell density can make predictions that are counter to biological intuition and experience including suggesting unrealistic fluctuations in cell density over small distances or predicting unlikely significant regions of high tumor cell density distant from the imageable component of the tumor.

The PI model has generalizability because it is a mechanistic model based on the underlying principles of tumor growth, but assumes cell density monotonically decreases from around the center of the tumor mass (i.e., enhancing core on a T1+C image) to the surrounding non-enhancing parenchyma (i.e., the so-called brain around the tumor (BAT)), not allowing significant local fluctuations. While it is generally true that higher cell densities are in the center of the imaging abnormality and the lower cell densities are on the outskirts, the monotonic nature limits the high resolution accuracy of the PI model estimates in BAT.

In one configuration of the present disclosure, a hybrid machine learning and mechanistic model, called ML-PI, is disclosed. This hybrid model integrates machine learning and PI models to increase accuracy in predicting intratumoral cell density distribution for a given patient.

In some implementations, the hybrid machine learning and mechanistic model adopts a semi-supervised learning (SSL) framework, which utilizes both biopsy samples (called labeled data) and biopsy-free sub-regions of the tumor (called unlabeled data). An SSL framework may be used in applications in which labeled data are scarce but unlabeled data are readily available and in a large quantity. In general, available biopsy samples are limited for each patient and there are abundant sub-regions of the tumor that are not biopsied, but with image features readily available.

There are many types of SSL algorithms, including generative, self-training, co-training, low-density separation, and graph-based models. In one configuration of the present disclosure, a graph-based SSL method is used to integrate PI with ML. Graph-based SSL has relatively high accuracy and efficiency. The basic idea is to construct a graph with vertices being labeled and unlabeled samples in a training set and edges weighted by vertex proximity in the feature space. There are two types of graph-based SSL: transductive and inductive learning models. The former aims to formulate a method to propagate label information from labeled samples to unlabeled samples in a specific dataset. In this way, the unlabeled samples in the dataset are classified/predicted. The latter aims to train a model using labeled and unlabeled samples, which is not only used to predict the unlabeled samples in training but also new samples.

Under a graph-based SSL framework, the hybrid machine learning and mechanistic models described in the present disclosure can incorporate biological feature data estimated by a mechanistic model (e.g., cell density data estimated with a PI model) to regularize a multiparametric MRI-based SSL model. The hybrid machine learning and mechanistic model is then able to learn patient-specific predictive relationships between imaging features and cell density that is superior to each modeling method alone. The resultant machine learning and mechanistic model improves the ability to capture substantial intra-patient and inter-patient heterogeneity.

As mentioned above, in some configurations of the present disclosure, a Relief-ML-PI algorithm can be implemented to quantify the contribution from each feature (e.g., each MRI sequence and PI) to the final cell density prediction. This algorithm can be used to examine feature contributions of the model post-training, as opposed to being used for feature selection pre-model training. Finding their respective contributions to prediction of tumor cell density helps knowledge discovery about GBM. Also, knowing the contribution from PI relative to imaging features reveals the importance of incorporating mechanistic models into data-driven machine learning.

Imbalance of labeled samples has been shown to significantly bias SSL models, in general. In one configuration, the data are naturally imbalanced with more samples concentrated toward the high end of the cell density spectrum than the low end, due to the ease of acquiring high-density samples in surgical biopsy. A data augmentation strategy may identify proper intratumoral regions from which to take "virtual" biopsy samples guided by PI. The augmented dataset contains balanced samples with density ranging from high to low, thus warranting good performance of the hybrid machine learning and mechanistic models described in the present disclosure.

As mentioned above, in some configurations, the hybrid ML-PI models described in the present disclosure can incorporate biological feature data estimated with a mechanistic model (e.g., PI-estimated regional cell density) into a graph-based SSL. The SSL framework is an extension of a classical supervised learning (SL) model, which may take the following form:

$$f^* = \underset{f \in H_K}{\operatorname{argmin}} \frac{1}{L} \sum_{l=1}^{L} (y_l - f(z_l))^2 + \gamma_A \|f\|_K^2; \quad (2)$$

where L is the number of biopsy samples in a training dataset; $y_l$ is the pathologically measured tumor cell density for the $l^{th}$ sample; $z_l$ contains features computed from a localized region of multiparametric MRI corresponding to the biopsy location; $f(z_l)$ is a predictive function for cell density; $(y_l - f(z_l))^2$ is a loss function that measures the discrepancy between the pathological and predicted density of each biopsy sample; $f$ is a function on the reproducing kernel Hilbert space ("RKHS"), $H_K$, with a Mercer kernel, K; $\|f\|_K^2$ is a norm on $H_K$, which encourages stability and generalizability of the solution; and $\gamma_A$ is a tuning parameter. In some configurations, the localized region may have a size of 8×8 voxels, which is roughly the size of biopsy samples in the image space.

Eqn. (2) is a supervised learning model because it uses the biopsy samples as labeled data. To incorporate unlabeled data and PI-estimated density into the model, a graph may be built on SSL with all labeled and unlabeled samples. For instance, one graph, G=(V, W), may be built for each patient, where V is the set of vertices and W contains the edge weight of the edge between each pair of vertices. Letting n=L+U be the number of vertices of the graph, where L is the number of all biopsy samples and U is the number of voxels on a pre-segmented tumoral ROI for the target patient (e.g., where the localized region for each voxel has a size of 8×8 voxels). The edge weight between vertices $v_i$ and $v_j$, for i,j=1, . . . , n can be computed using a product of two Gaussian functions as, $$w_{ij} = w_{ij,z} \times w_{ij,PI} = \exp\left(-\frac{\|z_i - z_j\|^2}{2\psi_z^2}\right) \times \exp\left(-\frac{(PI_i - PI_j)^2}{2\psi_{PI}^2}\right); \quad (3)$$

where $PI_i$ is PI-estimated cell density averaged over all the voxels in the localized region, and $\psi_z$ and $\psi_{PI}$ are parameters to adjust contributions to the weight from image features and PI, respectively. In other instances, the PI-estimated cell density in Eqn. (3) can be replaced with other biological feature data values depending on the mechanistic model used and the biological feature data to be estimated. In essence, $w_{ij}$ reflects the closeness between two samples/vertices in terms of their respective image features, $w_{ij,z}$ and PI estimations, $w_{ij,PI}$.

In addition to tuning the values of $\psi_z$ and $\psi_{PI}$, graph sparsification may be used for improving prediction accuracy and computational efficiency of the hybrid machine learning and mechanistic model. Sparsification of a graph, G(V, W), may include two steps. First, an edge between vertices $v_i$ and $v_j$ is kept if the edge weight is greater than a selected value, such as $w_{ij} > \varepsilon$. The edge between these vertices is otherwise removed. The remaining edges are then reweighted using Eqn. (3). Sufficient connectedness of the labeled biopsy instances with the unlabeled instances in the graph may ensure proper label diffusion (i.e., having non-zero $w_{ij}$ values, where, without loss of generality, i is a labeled instance and j is an unlabeled instance). It is contemplated that choosing a value of $\varepsilon$ such that 5-15% of the labeled instances are connected may produce high accuracy results.

The resultant, sparsified graph, $G_s = (V, W_s)$ can then be encoded into a Laplacian matrix, which may be defined as $\Omega = D - W$, where D is the vertex degree matrix, which can be a diagonal matrix with diagonal elements being the total sum of edge weights associated with each vertex, and W is the matrix of all the edge weights. Then, the model in Eqn. (2) can be augmented by incorporating the graph Laplacian matrix, which gives the proposed hybrid machine learning and mechanistic model as, $$f^* = \underset{f \in H_K}{\operatorname{argmin}} \frac{1}{L} \sum_{l=1}^{L} (y_l - f(x_l))^2 + \gamma_A \|f\|_K^2 + \frac{\gamma_I}{\sum_{i,j} w_{ij}} f^T \Omega f; \quad (4)$$

where $x_i = (z_i, PI_i)$; f contains predictive density (or other biological feature data) for each labeled and unlabeled sample, i.e., $f = (f(x_1), \ldots, f(x_L), f(x_{L+1}), \ldots, f(x_{L+U}))^T$;

$$\sum_{i,j} w_{ij}$$

is a sum of all the edge weights in the graph; and $\gamma_I$ is another tuning parameter. Because of patient heterogeneity, the graph of each patient may have a wide range of sparsity levels, which may cause difficulty in choosing a common search range for the tuning parameter, $\gamma_I$. Adding the sum, $$\sum_{i,j} w_{ij}$$

addresses this problem by normalizing each patient-specific graphs to allow for $\gamma_I$ to be tuned within a common range.

Through some algebra, the last term in Eqn. (4) can be described as, $$f^T \Omega f = \sum_{i,j=1}^{L+U} (f(x_i) - f(x_j))^2 w_{ij,z} \times w_{ij,PI}. \quad (5)$$

With this change, it can be seen that the minimization in Eqn. (4) pushes samples that are closer in image features (i.e., with a larger $w_{ij,z}$) and in PI estimations (i.e., with a larger $w_{ij,PI}$) to have more similar predictions. This is traded off with the loss on the labeled data (i.e., the first term in Eqn. (4)) and the smoothness of the predictive function in RKHS (i.e., the second term in Eqn. (4)). In the extreme case when $w_{ij,z}=w_{ij,PI}=0$ for all the edges, Eqn. (4) becomes the supervised learning model in Eqn. (2). In essence, the role of PI in the proposed model is to regularize the learning of the predictive function in order to make sure the spatial proximity of predicted densities conform with that of PI densities to some extent. This implicitly takes into account the bio-mechanism of tumor growth, which is the foundation of the PI model.

The Representer Theorem can be used to show that an analytical solution for Eqn. (4) exists in $H_K$. The solution of the optimization in Eqn. (4) can be written as the following expansion in terms of both labeled and unlabeled samples:

$$f^*(x) = \sum_{i=1}^{L+U} \alpha_i K(x_i, x); \quad (6)$$

where X is any sample for which the cell density is to be predicted, which can be an unlabeled sample included in the hybrid machine learning and mechanistic model in Eqn. (4) or not (e.g., a sample outside the ROI or on a different slice of the tumor), and $\alpha_i$ are coefficients.

With the form of the solution to Eqn. (4), the coefficients, $\alpha_i$ need to be estimated. To achieve this, Eqn. (6) can be inserted into Eqn. (4), in order to obtain the following convex differentiable objective function of $\alpha=[\alpha_1 \ldots \alpha_{L+U}]^T$:

$$\alpha^* = \operatorname{argmin} \frac{1}{L}(y - JK\alpha)^T(y - JK\alpha) + \gamma_A \alpha^T K\alpha + \frac{\gamma_I}{\sum_{i,j} w_{ij}} \alpha^T K\Omega K\alpha; \quad (7)$$

where J is an (L+U)×(L+U) diagonal matrix in which the first L entries are 1s and the rest are 0s, K is an (L+U)×(L+U) Gram matrix over labeled and unlabeled samples, y is an (L+U)×1 vector defined by $y=[y_1 \ldots y_L, 0 \ldots 0]^T$. Furthermore, taking the derivative with respect to $\alpha$, the following expression is obtained:

$$\frac{1}{L}(y - JK\alpha)^T(-JK) + \left(\gamma_A K + \frac{\gamma_I L}{\sum_{i,j} w_{ij}} K\Omega K\right)\alpha = 0. \quad (8)$$

Solving for $\alpha$ yields a solution as, $$\alpha^* = \left(JK + \gamma_A LI + \frac{\gamma_I L}{\sum_{i,j} w_{ij}} \Omega K\right)^{-1} y; \quad (9)$$

Where I is an (L+U)×(L+U) identity matrix. Inserting the coefficient, $\alpha_i$, obtained above into Eqn. (5), the predictive function, $f^*(x)$, is obtained. This predictive function can be used to generate a predicted cell density for every voxel within the ROI and thus can be used to form an intratumoral cell density map. The tuning parameters of Eqn. (4)—namely, $\gamma_A$, $\gamma_I$, and $\eta$, the latter of which is the width of the radial basis function kernel, $K(x_i,x_j)=\exp(-\|x_i-x_j\|^2/2\eta^2)$—can then be adjusted to find the value for $f^*(x)$ that maximizes the accuracy of the hybrid machine learning and mechanistic model.

FIG. 1 illustrates an example flowchart of a hybrid machine learning and mechanistic model (e.g., an ML-PI model). First, the machine learning and mechanistic models take as input image-localized biopsies and multiparametric MRI to make predictions of tumor cell density. In FIG. 1, the cell density maps show predictions of low density (blue) to high density (red). The hybrid machine learning and mechanistic model then encodes similarities between voxel intensities of the mechanistic model into a Laplacian matrix, $\Omega$, which is used to help regulate prediction in the training of the machine learning model.

In one configuration, a transfer learning approach can also be implemented. Transfer learning (TL) blends the two approaches mentioned above by first building a Bayesian framework from predominant trends in group analysis and then transferring these prior distributions, through a process called domain selection, to construct individual models for each patient that are tuned according to that patient's specific MRI and histologic data.

A transfer learning routine may be selected from various forms, such as:

$$\hat{W}^I = \operatorname*{argmin}_{W} \left\{ \sum_{k=1}^{K} \|y_k - X_k w_k\|_2^2 + \lambda_1 \|W\|_1 + \lambda_2 (Q\log|\Omega| + tr(LW\Omega^{-1}W^T)) \right\}; \quad (10)$$

where $W=(w_1, \ldots, w_K)$, and $\hat{W}$ is a Bayesian MAP estimate for W; $y_k$ and $X_k$ denote the data for the response and predictors of the k-th domain $k=1, \ldots, K$; $\|\ldots\|_2^2$ and $\|\ldots\|_1$ denote the L1-norm and L2-norm, respectively; $\lambda_1=2\sigma^2/b$ and $\lambda_2=\sigma^2$; $\lambda_1 \geq 0$ and $\lambda_2 \geq 0$ serve as regularization parameters to control the sparsity of $\hat{W}$ and the amount of prior knowledge used for estimating W; and the hyper-parameter $\Omega$ is a matrix of potentially high dimensionality that encodes the prior knowledge about the correlation structure between domains. For each domain, k, there is a model that links X to Y by coefficients $w_k$.

Another structure for a transfer learning routine may include:

$$\hat{W}^{II} = \operatorname*{argmin}_{w_K} \left\{ \|y_k - X_k w_k\|_2^2 + \lambda_1 \|w_K\|_1 + \lambda_2 \left( \begin{array}{c} Q\log(\zeta_K - \varpi_K^T \hat{\Omega}^{-1} \varpi_K) + \\ \frac{1}{\zeta_K - \varpi_K^T \hat{\Omega}^{-1} \varpi_K}(w_K - \mu_K)^T L(w_K - \mu_K) \end{array} \right) \right\} \quad (11);$$

$$\text{where } \Omega = \begin{pmatrix} \hat{\Omega} & \varpi_K \\ \varpi_K^T & \zeta_K \end{pmatrix}.$$

Still another structure for a transfer learning routine may include:

$$(\hat{W}^{III}, \hat{\Omega}^{III}) = \underset{W,\Omega}{\operatorname{argmin}} \left\{ \left\{ \sum_{k=1}^{K} \|y_k - X_k w_k\|_2^2 + \right.\right. \quad (12);$$

$$\left.\left. \lambda_1 \|W\|_1 + \lambda_2 (Q \log|\Omega| + tr(LW\Omega^{-1}W^T)) \right\} \right\}$$

where $\hat{\Omega} = \dfrac{w^T L w}{Q}$.

In one non-limiting example, one model is built for each patient to account for potential patient differences while coupling the estimation processes of the patient-specific models to allow for knowledge transfer between the models. Specifically, suppose there are N patients in the training dataset. A linear model may be established between imaging features and cell density for patient, k, such as, $$y_k = X_k w_k + \varepsilon_k \text{ for } k=1, \ldots, N \quad (13);$$

where $y_k$ are the cell density measurements for $n_k$ biopsy samples, $X_k$ are the MRI features for the biopsy samples, $w_k$ are the model coefficients yet to be estimated, and $\varepsilon_k$ are random errors following a Gaussian distribution. The original cell density measurement, which is between 0 and 1, may be transferred using a suitable function, such as a sigmoid function. Furthermore, to couple the models from different patients, a Bayesian framework may be adopted. It can also be assumed that the patient-specific model coefficients, $W=w_1, \ldots, w_N$, share the same prior distribution, i.e., $$p(W \mid \Omega, \Phi, b) \propto \prod_{k=1}^{K} Laplace(w_k, b) \times MN(W; 0, \Omega, I); \quad (14)$$

where Laplace($w_k$;b) is a Laplace distribution to facilitate sparsity in model estimation (i.e., to produce a parsimonious model for better interpretability), and MN(W;0, $\Omega$,I) is a zero-mean matrix-variate normal distribution. Specifically, the covariance matrix, $\Omega$, encodes the correlation between different patients.

Furthermore, given the prior distribution in Eqn. (14), and the likelihood based on the training data, $p(y_k\|X_k,w_k) \sim N(y_k; X_k w_k, \sigma^2 I)$, the posterior distribution of W can be obtained as, $$p(W \mid \{y_k, X_k\}_{k=1}^{K}, \Omega, \Phi, b) \propto p(W \mid \Omega, \Phi, b) \prod_{k=1}^{K} p(y_k \mid X_k, w_k). \quad (15)$$

Then, the maximum a priori ("MAP") estimator for W can be obtained by solving the following optimization problem, $$\hat{W} = \underset{W,\Omega}{\operatorname{argmin}} \left\{ \sum_{k=1}^{N} \|y_k - X_k w_k\|_2^2 + \right. \quad (16)$$

$$\left. \lambda_1 \|W\|_1 + \lambda_2 (Q \log|\Omega| + tr(W\Omega^{-1}W^T)) \right\};$$

where $\| \ldots \|_2^2$ and $\| \ldots \|_1$ denote the L1-norm and L2-norm, respectively; and $\lambda_1 \geq 0$ and $\lambda_2 \geq 0$ are two regularization parameters that control the sparsity and the amount of knowledge transferred between the models of different patients, respectively. The parameters $\lambda_1$ and $\lambda_2$ can be selected to maximize the leave-one-out-cross-validation (LOOCV) accuracy. LOOCV may be used to reduce overfitting. Alternatively, other approaches for reducing overfitting can be used, such as using dropouts or other regularizations.

Eqn. (16) is a transfer learning model in the sense that it allows a joint estimation of patient-specific model coefficients, $w_k$ for k=1, . . . , N. An advantage of the transfer model in Eqn. (16) is that it does not require a pre-specification on the correlation between patients, $\Omega$, but can estimate it in a data-driven manner. To solve the optimization problem in Eqn. (16) (i.e., to estimate W and $\Omega$), an efficient alternating algorithm that estimates W and $\Omega$ can be implemented. That is, given $\Omega$, the optimization problem with respect to W is convex and may be solved using the accelerated gradient algorithm. Given W, $\Omega$ can be solved analytically.

Figure 2:
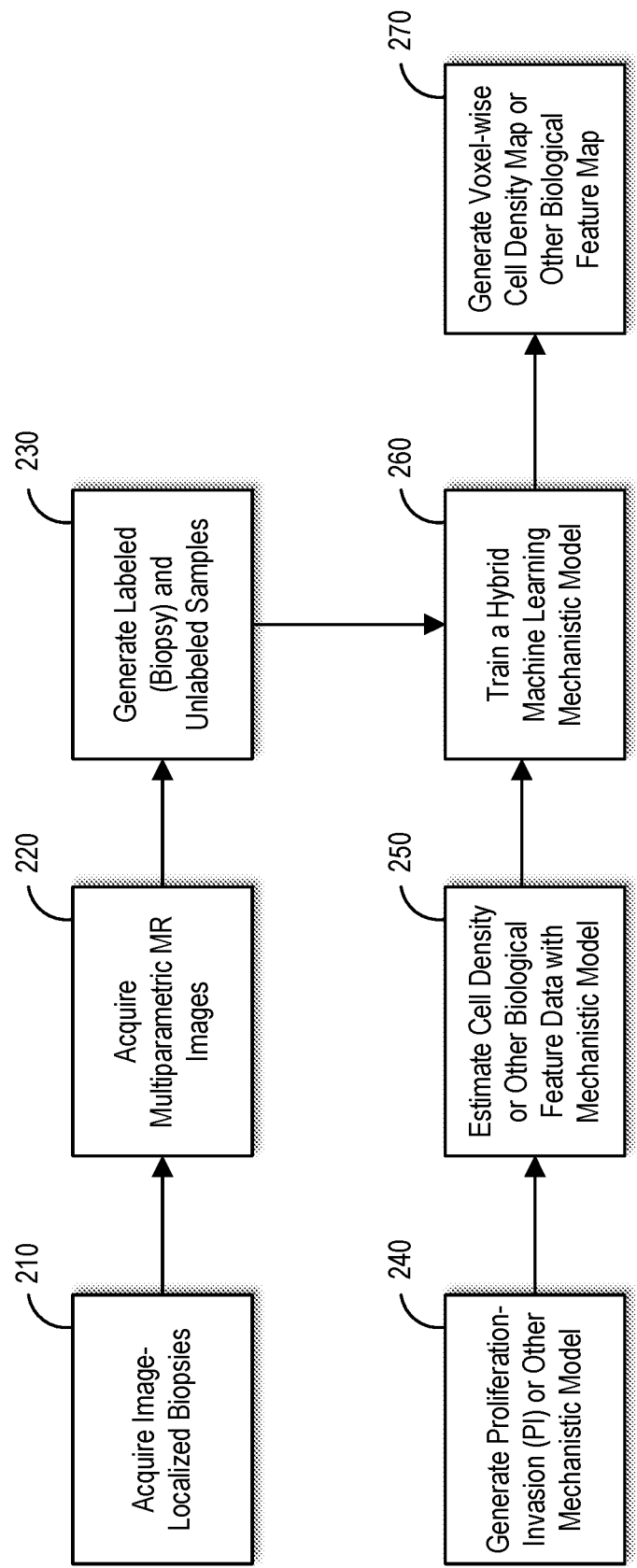
FIG. 2 is a flowchart of one non-limiting example process according to the present disclosure.

Referring now to FIG. 2, a flowchart is illustrated as setting forth a non-limiting example of generating and implementing a hybrid machine learning and mechanistic model to produce biological feature maps (e.g., cell density maps), or otherwise measure or predict one or more biological features (e.g., cell density), based on input multi-parametric magnetic resonance images. Three types of input may be used to train a hybrid machine learning and mechanistic model, including image-localized biopsies acquired at step 210, multiparametric MRI acquired at step 220, and a biological feature map (e.g., a cell density map) generated at step 250. As one example, the biological feature map can be a cell density map, such as a cell density map generated by a PI model generated or otherwise provided at step 240. In general, the PI model simulates tumor cell proliferation and invasion using partial differential equations. As noted above, other mechanistic models can also be used to model other biological and/or physiological processed and to generate other biological feature data.

The image-localized biopsies acquired at step 210 may be T2-weighted images, T1-weighted images acquired with a contrast agent, or any other suitable magnetic resonance image, parametric map generated from magnetic resonance images (e.g., fractional anisotropy maps, relative cerebral blood volume maps), and so on. The multiparametric MR images acquired at step 220 may include T2-weighted images, T1-weighted images acquired with a contrast agent, images acquired with an echo-planar imaging (EPI) pulse sequence and with a contrast agent, mean diffusivity (MD), fractional anisotropy (FA), relative cerebral blood volume (rCBV), and the like.

For instance, in a glioma patient cohort, various MRI sequences containing complementary information may be used to assist clinical decision making, including T1-weighted imaging, which can depict bulk tumor and blood-brain-barrier disruption; T2-weighted imaging, which can depict non-specific region surrounding; diffusion tensor imaging (DTI), which can be used to measure white matter infiltration; and perfusion imaging, which can be used to measure microvessel morphology. The rCBV metric, which can be computed based on images obtained with perfusion imaging, may be used as a marker of microvessel blood volume on T2 perfusion MRI. Mean Diffusivity (MD) may be used to image bulk water movement measured on DTI and may be a marker of cell density. Fractional Anisotropy (FA) may provide for directional water movement measured on DTI and may be a marker of white matter integrity/invasion. EPI+contrast may also be a marker of cell density. Mapping intratumoral cell density distribution can take advantage of multi-sequence or multiparametric MRI.

Labeled samples, which may be biopsy samples, and unlabeled samples are generated at step 230. These inputs may be integrated under a graph-based semi-supervised learning (SSL) framework to train a predictive function at step 260 between localized MRI features and one or more biological features, such as cell density.

In the ML-PI integration, biopsy samples are used to minimize the error between predicted and pathological cell density (considered as ground truth). The PI map and multiparametric magnetic resonance images are converted to a graph Laplacian matrix, $\Omega$, which encodes the similarities between voxel intensities in the multivariate space (PI and multiparametric magnetic resonance images) to regularize the predictive function of ML-PI. Once the predictive function is estimated, it can be used to generate a cell density map at step 270 for spatial distribution of low cell density to high density within a region-of-interest (ROI) using localized MRI features. As described above, this process can be adapted to integrate mechanistic models other than a PI model and to estimate biological features other than cell density.

The quantitative contribution of each feature (e.g., imaging features and PI-estimated density, other biological features) may be determined for its contribution to the prediction made by the hybrid machine learning and mechanistic model (e.g., a hybrid ML-PI model). All of the included MRI sequences and PI are biologically relevant to tumor cell density. Therefore, inclusion of them as features in building the ML-PI model may be valuable, while their relative contributions may vary. In one configuration of the present disclosure, instead of employing feature selection (e.g., a step prior to building a predictive model with purpose of removing irrelevant features), a post-processing step that identifies how much each feature contributes to the prediction may be used.

For instance, let X be a feature used in the hybrid machine learning and mechanistic model (e.g., ML-PI model), which can be a feature computed from an MRI sequence or biological feature data (e.g., PI-estimated cell density). A score, s(x), for that feature, X, which represents the contribution of that feature, may be computed. As mentioned above, in some implementations these contributions can be quantified by adapting a Relief algorithm, which was originally developed as a feature selection algorithm for supervised learning models. In one configuration of the present disclosure, the adapted Relief algorithm is used a post-analysis algorithm for feature contribution analysis of the hybrid machine learning and mechanistic models described in the present disclosure. The score, s(x), of a feature can be defined as follows. The training data, T, from which the hybrid machine learning and mechanistic model has been built includes both labeled and unlabeled samples, as described above. Letting i and $i_r$ be samples in the training data, T, $i_r$ is the $r^{th}$ nearest neighbor of i on the graph, G. Furthermore, the predicted biological feature data (e.g., cell density) of the two samples by the hybrid machine learning and mechanistic model can be referred to as $\hat{y}_i$ and $\hat{y}_{i_r}$, and their respective measurements on the feature, X, can be referred to as $x_i$ and $x_{i_r}$. The definition of the score, s(x), can be based on the difference between two probabilities as, $$s(x) = P(x_i \text{ and } x_{i_r} \text{ are different} | \hat{y}_i \text{ and } \hat{y}_{i_r} \text{ are different}) - \qquad (17)$$
$$P(x_i \text{ and } x_{i_r} \text{ are different} | \hat{y}_i \text{ and } \hat{y}_{i_r} \text{ are similar}).$$

The first term represents the probability that the feature, X, is able to separate samples with different prediction values, while the second term represents the probability that the feature, X, separates samples with similar prediction values. The larger the first probability and the smaller the second, the higher the value of the score, s(x). Furthermore, using Bayes' rule, Eqn. (17) can be written as, $$s(x) = \frac{P(\hat{y}_i \text{ and } \hat{y}_{i_r} \text{ are } diff. | x_i \text{ and } x_{i_r} \text{ are } diff.) \times P(x_i \text{ and } x_{i_r} \text{ are } diff.)}{P(\hat{y}_i \text{ and } \hat{y}_{i_r} \text{ are } diff.)} - \qquad (18)$$

$$\frac{\{1 - P(\hat{y}_i \text{ and } \hat{y}_{i_r} \text{ are } diff. | x_i \text{ and } x_{i_r} \text{ are } diff.)\} \times P(x_i \text{ and } x_{i_r} \text{ are } diff.)}{1 - P(\hat{y}_i \text{ and } \hat{y}_{i_r} \text{ are } diff.)}$$

The format of s(x) in Eqn. (18) makes it relatively easier than Eqn. (17) to develop an algorithm to estimate s(x). For instance, m samples can be randomly selected from the training data, T. For each sample, its k nearest neighbors $i_r$, r=1, . . . , k, are

---

Algorithm 1 Example Relief-ML-PI

Input: measurement data $x_i$ and predicted response $\hat{y}_i$ for each sample in training set T; tuning parameters m, k.
Output: s(x)
1:    Initialize:
2:       $s(x) \leftarrow 0$; $N_{dy}(x) \leftarrow 0$; $N_{dx}(x) \leftarrow 0$; $N_{dy\&dx}(x) \leftarrow 0$;
3:    for i = 1 to m do
4:       Randomly select a sample i from T;
5:       Find k nearest neighbors for sample i, $i_1, \ldots, i_k$ on graph G;
6:       for r = 1 to k do
7:          $N_{dy}(x) \leftarrow N_{dy}(x) + d(\hat{y}_i, \hat{y}_{i_r}) \times \delta(i, i_r)$;
8:          $N_{dx}(x) \leftarrow N_{dx}(x) + d(x_i, x_{i_r}) \times \delta(i, i_r)$;
9:          $N_{dy\&dx}(x) \leftarrow N_{dy\&dx}(x) + \delta(\hat{y}_i, \hat{y}_{i_r}) \times d(x_i, x_{i_r}) \times \delta(i, i_r)$;
10:      end for
11:   end for
12:   $s(x) \leftarrow \frac{N_{dy\&dx}(x)}{N_{dy}(x)} - \frac{N_{dx}(x) - N_{dy\&dx}(x)}{m - N_{dy}(x)}$;

--- found. Then, the probabilities in Eqn. (18) are estimated in order to estimate the score, s(x) using lines 7-9 of the following algorithm, in which $$d(\hat{y}_i, \hat{y}_{i_r}) = \frac{|\hat{y}_i - \hat{y}_{i_r}|}{\max(\hat{y}_j | j \in T) - \min(\hat{y}_j | j \in T)},$$

$$d(x_i, x_{i_r}) = \frac{|x_i - x_{i_r}|}{\max(x_j | j \in T) - \min(x_j | j \in T)},$$

as the normalized difference between the response variables or feature values of two samples, and $$\delta(i, i_r) = \frac{\delta'(i, i_r)}{\sum_{i=1}^{k} \delta'(i, i_r)}, \delta'(i, i_r) = e^{-\left(\frac{rank(i,i_r)}{\sigma}\right)^2}.$$

$\delta'(i, i_r)$ weights each of the k nearest neighbors for sample i and $\delta(i, i_r)$ normalizes the weights. The rank of the k nearest neighbors may be used instead of computing the numerical distance to make sure different samples are equally accounted for.

In some configurations, the biopsy samples used to build the ML-PI model may be biased toward high cell density. For example, in one example study, a dataset was used in which there was a concentration of samples above 50% density with mean density equal to 63%. The imbalance of biopsy samples toward higher densities may be because of inherent difficulty in acquiring low-density samples. This imbalance can create bias in model training, i.e., it will tend to train a model that over-predicts cell density of any given sample.

To address this issue, in some instance low density samples can be weighted more than high density samples. However, the ML-PI model aims to predict the numerical density on a continuous scale, for which sample weighting is not straightforward, so this implementation may not be the most convenient in all instances. Alternatively, the biopsy samples of each patient can be augmented with "virtual" biopsy samples, for which the density measurement takes the value generated from PI. In this way, an augmented dataset that contains balanced samples with density ranging from high to low can be generated and used.

Because the PI-estimated density of each virtual biopsy sample will be treated the same as pathologically measured density, the locations of the virtual biopsies can be preferentially be selected as those where PI estimations are accurate. In some instances, a procedure is provided to guide virtual biopsy site selection according to both biological and statistical criteria. Purposes of the biological criteria are to avoid certain anatomical structures of the brain (e.g., skull, midline) where PI estimation is known to be inaccurate and to appeal to certain sub-areas of the tumor where PI estimation is highly likely to be accurate. Statistical criteria include considerations on the spatial consistency of PI estimations and on properties of the virtual biopsy samples in the feature space to facilitate statistical model estimation.

Combining imaging data with mathematical models of brain tumor proliferation integrates the advantages of having empirical information from images with scientific knowledge of the underlying cellular mechanisms of tumor growth. Glioblastoma ranks among the most lethal of all human cancers. Poor survival is largely attributed to tumoral invasion and intratumoral heterogeneity (sub-regions within the same tumor having different molecular signatures and therapeutic sensitivities).

The hybrid models described in the present disclosure, which integrate machine learning built from multiparametric MRI features with mechanistic models of biological or physiological processes (e.g., tumor invasion, which may be modeled using a proliferation-invasion, PI, mechanistic model), may increase accuracy in predicting regional biological features (e.g., tumor cell density) for each patient. As described above, imaging data-driven machine learning (e.g., graph-based semi-supervised learning) may be integrated with mechanistic models. Biopsy samples used in training these hybrid machine learning and mechanistic model(s) may be augmented with virtual biopsy samples guided by PI, effectively tackling sample imbalance and improving statistical learning power. In some instances, a Relief-ML-PI, adapted from the Relief algorithm, may be used to perform post-analysis to quantify contributions from different MRI sequences and PI, which may advance model validation and promote understanding of tumor bio-physiology.

In one example study, the ML-PI framework described in the present disclosure was implement to generate cell density maps for a clinical cohort of primary GBM patients undergoing surgical biopsy and resection. In this study, a high accuracy in cell density prediction was achieved in comparison with competing methods. PI was found to contribute most significantly to the prediction, followed by MRI sequences T1+C, FA, T2W, rCBV, all of which were shown relevant to cell density in existing imaging studies. Predicted cell density maps were generated for each patient across the tumor mass and BAT, allowing for precision treatment.

Patients were recruited with clinically suspected glioma undergoing preoperative stereotactic multi-parametric MRI for surgical biopsy and/or resection. The absence of previous treatment was confirmed. Approval was obtained from the institutional review boards and informed consent was obtained from each subject prior to enrollment. 82 biopsy samples were collected from 18 glioma patients, with each patient having 2-14 biopsy samples.

Six multiparametric images were included in the study, including T1+C, T2W, EPI+C, MD, FA, and rCBV. Cell density predictions were generated for the abnormality shown on T2W (called T2W ROI hereafter), which includes both the tumor mass enhanced on T1+C and non-enhanced BAT. The latter is known to harbor residual tumor cells after resection, which lead to treatment failure and recurrence. The T2W ROI of each tumor was manually segmented by a board-certified neuroradiologist.

An 8×8 voxel box was placed at the location of co-registered images that corresponded to each biopsy sample. The average gray-level intensity over the 64 voxels within the box was computed for each image sequence. In addition to computing features for the biopsy samples (i.e., labeled samples), features were also computed for unlabeled samples in the following way. One slice of MRI was chosen for each patient, which is approximately the cross-section that included a balanced amount of enhancing mass and non-enhancing BAT. Furthermore, 8×8 voxel boxes were placed one pixel apart on the T2W ROI, and the same image features as those of the biopsy samples were computed for each box.

Using the T1+C and T2W images of each patient as input, voxel-wise density estimation was generated by the PI model. Average PI density over the pixels in each 8×8 box on the selected slice was computed.

To provide a balanced dataset for ML-PI model training, virtual biopsies were identified for each patient (if necessary) to balance the high density samples with "virtual" low density samples according to the steps described above. A total of 39 virtual biopsy samples were added with each patient having 0-6 samples. The histogram of pathological density for the real biopsy samples in the dataset used in this study indicated a clear imbalance toward high density. A histogram of augmented samples indicated good balance. Furthermore, for each virtual biopsy sample, the same approach was used to compute imaging features and average PI density as was used for real biopsy samples. Virtual biopsy samples were used in model training.

The virtual biopsy selection method for each patient included the following procedure. The number of biopsy samples with density greater than 70% was selected and denoted as r. The number of real biopsies with low-density was denoted as r'. The number of virtual biopsy samples with low-density (e.g., less than 30%) that were to be found, in order to create balanced samples for the patient, was computed as v=r−r'. The BAT for the patient was located by subtracting the ROI segmented on T1+C from the ROI segmented on T2W. On the PI-estimated density map over the BAT, a sub-area from which to take the virtual biopsy was selected according to a set of biological criteria. As one example, the following biological criteria were used: (1) the sub-area needs to be away from the skull and the midline of the brain, since PI estimation tends to be less accurate at locations with physical barriers; and (2) the sub-area should be close to the peripheral of the T2W ROI, where there is much lower chance to harbor high cell density.

Considering spatial continuity of cell density distribution, the PI estimation at a neighborhood of the biopsy sample should be more likely to be accurate if there is a real biopsy sample with low density whose PI density is also low. If the density of the real biopsy sample disagrees with PI density, the neighborhood of the sample should be avoided.

On the sub-area that was picked, the following statistical criteria were further applied to select virtual biopsy samples. First, the spatial consistency of PI density was considered. For each pixel in the sub-area, an 8×8 voxel box was placed around it. Then, the mean and variance of PI densities over the 64 pixels within the box were computed. The boxes with a low mean (e.g., less than 30%) and a low variance were retained as potential virtual biopsy samples. Next, separation in the imaging feature space was considered. Good virtual biopsy samples should be at a certain distance away from each other in the input (imaging features) space (called leverage samples in statistics) in order to stabilize model fitting. To find the leverage samples, a highly flexible and efficient clustering algorithm (e.g., DBSCAN) can be used to cluster the boxes that have survived using imaging features. Parameters of DBSCAN are set to produce approximately v clusters. Then, one box from each cluster was picked as the virtual biopsy sample.

For real biopsies, pre-operative conventional MRI, including T1-weighted contrast-enhanced (T1+C) and T2-weighted sequences (T2W), was used to guide biopsy selection. Each neurosurgeon collected an average of 5-6 tissue specimens from each tumor by using stereotactic surgical localization, following the smallest possible diameter craniotomies to minimize brain shift. Specimens were collected from both enhancing mass (as seen on T1+C) and non-enhancing BAT (as seen on T2W) for each tumor. The neurosurgeons recorded biopsy locations via screen capture to allow subsequent coregistration with multiparametric MRI datasets. The biopsy tissue specimens were reviewed blinded to diagnosis by a neuropathologist and assessed for tumor content. Taking into account all visible cells (neurons, inflammatory cells, reactive glia, tumor cells, etc.), the percent tumor nuclei were estimated.

Before applying ML-PI, a graph was constructed for each patient/tumor (called target patient hereafter). Vertices of the graph corresponded to boxes placed on the T2W ROI of the selected slice for the target patient as well as biopsy samples from other patients. As described above, the ML-PI model includes three parameters that can be tuned: $\gamma_A$, $\gamma_I$, and $\eta$. The tuning parameter $\eta$ is the width of the radial basis function kernel, $$K(x_i, x_j) = e^{-\|x_i - x_j\|^2 / 2\eta^2}.$$

The tuning ranges used were $\gamma_I$, $\gamma_A \in \{10^{-10}, \ldots, 10^4\}$; $\eta \in \{10^{-1}, \ldots, 10^2\}$. Two tuning strategies were compared in this example study: patient-specific tuning and uniform tuning. The former finds the optimal tuning parameters for each patient while the latter assumes the same optimal tuning parameters across all patients.

In patient-specific tuning, an ML-PI model was trained for each patient using the augmented biopsy samples from other patients in the loss term. No real or virtual biopsy samples from the target patient were used in training in order to avoid overfitting. Then, the trained model was used to predict the real biopsy samples of the target patient. The optimal tuning parameters were those that minimized the mean absolute prediction error (MAPE) of the target patient. In uniform tuning, a single set of tuning parameters that minimized the MAPE across all patients was looked for. Theoretically, uniform tuning should perform no better than patient-specific tuning.

Figures 3A, 3B:
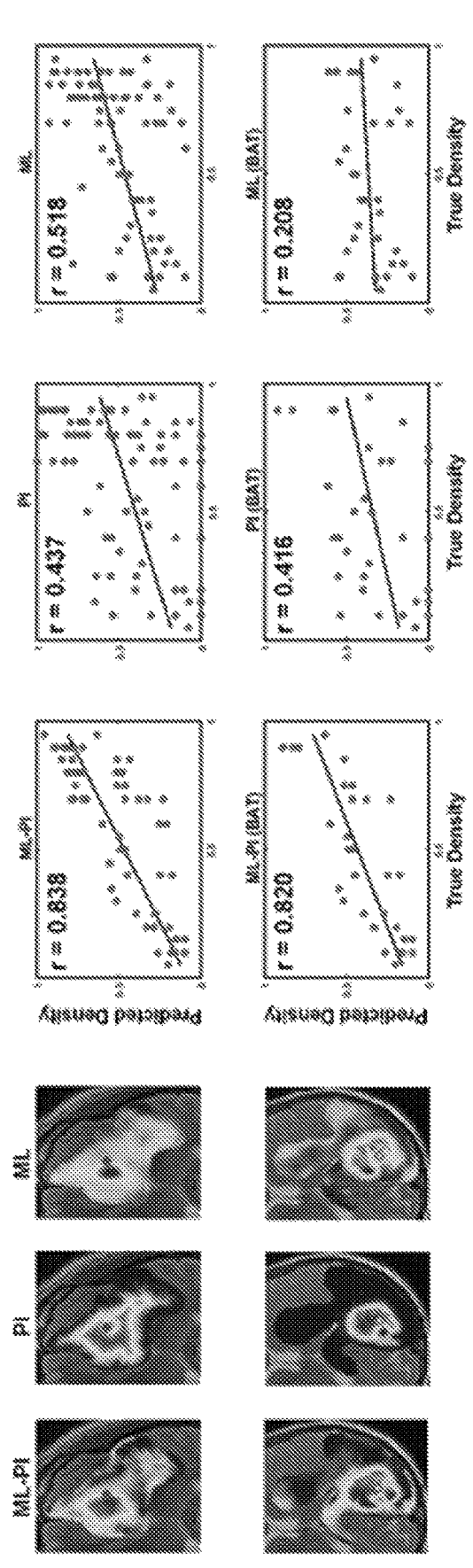
FIGS. 3A and 3B depict non-limiting examples of predicted cell density maps (FIG. 3A) and predicted cell density by ML-PI, PI mechanistic model, and ML shown against pathological density for 82 biopsy samples (FIG. 3B).

Referring to FIG. 3A, examples of non-limiting predicted cell density maps are shown overlaid on T2W image for two patients (8 and 16) by three different models. Gradation in the contrast represents 100%-0% density. A circle indicates location of a biopsy sample. For patient 8, the pathological density of the biopsy is 90% and predicted densities by ML-PI, PI, and ML are 79.0%, 59.2%, and 56.4%, respectively. For patient 16, the pathological density of the biopsy is 70% and predicted densities by ML-PI, PI, and ML are 79.4%, 82.9%, and 54.9%, respectively.

Referring to FIG. 3B, examples of non-limiting predicted density by ML-PI, PI, and ML are shown against pathological density for 82 biopsy samples; predicted density by ML-PI, PI, and ML are also shown against pathological density for 33 biopsy samples in non-enhancing (BAT) region. Additionally, r denotes the Pearson correlation coefficient.

The effect of the three tuning parameters on model accuracy when allowed to be patient-specific was also investigated in this example study. A third tuning strategy was added to facilitate these comparisons. This third tuning strategy was referred to as partially-uniform tuning, in which two of the three tuning parameters were kept the same across all patients while the remaining one was allowed to vary from patient to patient. This resulted in three models corresponding to $\gamma_A$, $\gamma_I$, or $\eta$ as the parameter allowed to be patient-specific, respectively. In general, patient-specific tuning of $\gamma_A$ resulted in a significantly improved MAPE and Pearson correlation (p=0.023 and 0.011). Patient-specific tuning of $\eta$ did not appear to result in a significantly improved MAPE and Pearson correlation, however the improvement of MAPE approached the 0.05 significance threshold (p=0.087 and 0.17). Patient-specific tuning of $\gamma_I$ did not appear to significantly improve the MAPE and Pearson correlation (p=0.22 and 0.35).

Based on these results, it is contemplated that patient-specific tuning of $\gamma_A$ alone may not significantly deteriorate the performance in terms of MAPE and Pearson correlation (p=0.14 and 0.39), while patient-specific tuning of $\eta$ alone shows a greater difference in MAPE and Pearson correlation (p=0.057 and 0.044) and $\gamma_I$ exhibits a significant deterioration in MAPE and Pearson correlation (p=0.012 and 0.014). These results indicate that $\gamma_I$ (and, to some extent, $\eta$) may require less sensitive tuning between patients, suggesting that the Laplacian matrix that incorporates PI similarities successfully accounts for patient differences (thus not necessitating the need for a patient-specific $\gamma_I$).

In one non-limiting example, a predicted cell density map was generated for the T2W ROI in order to guide neurosurgery and radiation therapy. In this experiment, the trained ML-PI model was used to predict tumor cell density on every 8×8 voxel box placed one pixel apart on the T2W ROI. This generated a predicted density map on the T2W ROI. ML-PI was able to predict a wider spread of density than PI alone, making it possible to capture high-density regions in the BAT.

Figure 4:
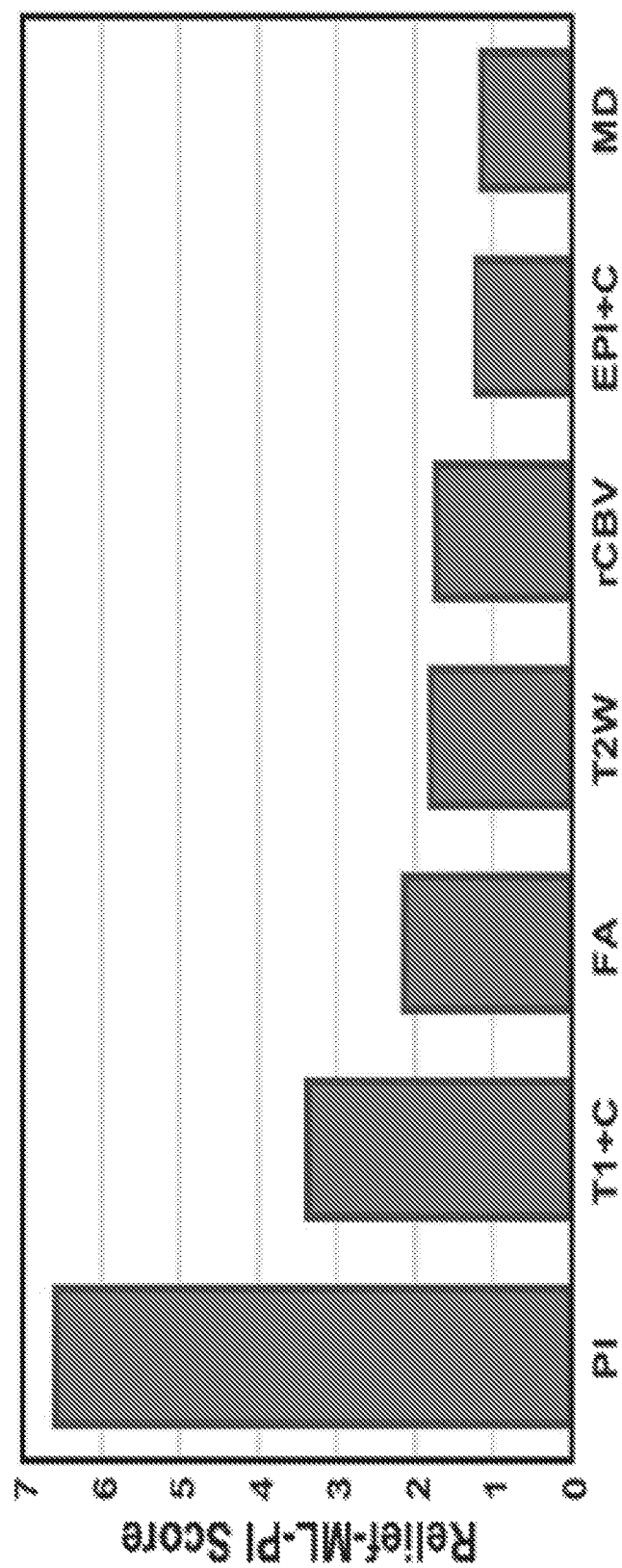
FIG. 4 depicts a non-limiting example of contributions of proliferation invasion (PI) and MRI sequences to machine learning proliferation-invasion (ML-PI) cell density prediction.

Referring to FIG. 4, an example of contributions of PI and MRI sequences to ML-PI cell density prediction is depicted. Using Relief-ML-PI, a contribution score was computed for each image feature (one feature per MRI sequence) and PI from the ML-PI model specific to each patient. In one non-limiting example, to identify the contributions aggregated over all the patients, the score was normalized for each feature within each patient to be between 0 and 1 by dividing the score by a sum over the scores of all the features. Then, the normalized scores from each patient were added together to produce an aggregated score showing contribution from each feature. From these results, it is contemplated that PI contributes the most, followed by T1+C, FA, T2, rCBV, all of which are relevant to cell density.

Thus, systems and methods are provided that utilize the above-described ML-PI model, for example, to use multi-parametric MRI and PI and to regularize tumor cell density prediction under a graph-based SSL framework. ML-PI had capabilities of learning patient-specific relationships between imaging features and cell density, and was found to have a greater prediction accuracy than ML or PI alone when applied to a GBM patient cohort from BNI/MCA. Additionally, ML-PI showed a more balanced prediction in the T2W ROIs when compared to PI, while the latter underestimated the cell density, indicating that ML-PI was more capable of capturing high density regions in BAT. The Relief-ML-PI technique can determine contributions of each individual feature to ML-PI prediction. PI contributed most significantly to the prediction, followed by MRI sequences rCBV and MD. This highlighted the utility of incorporating mechanistic models in the form of PI to help improve tumor cell density prediction.

Figure 5:
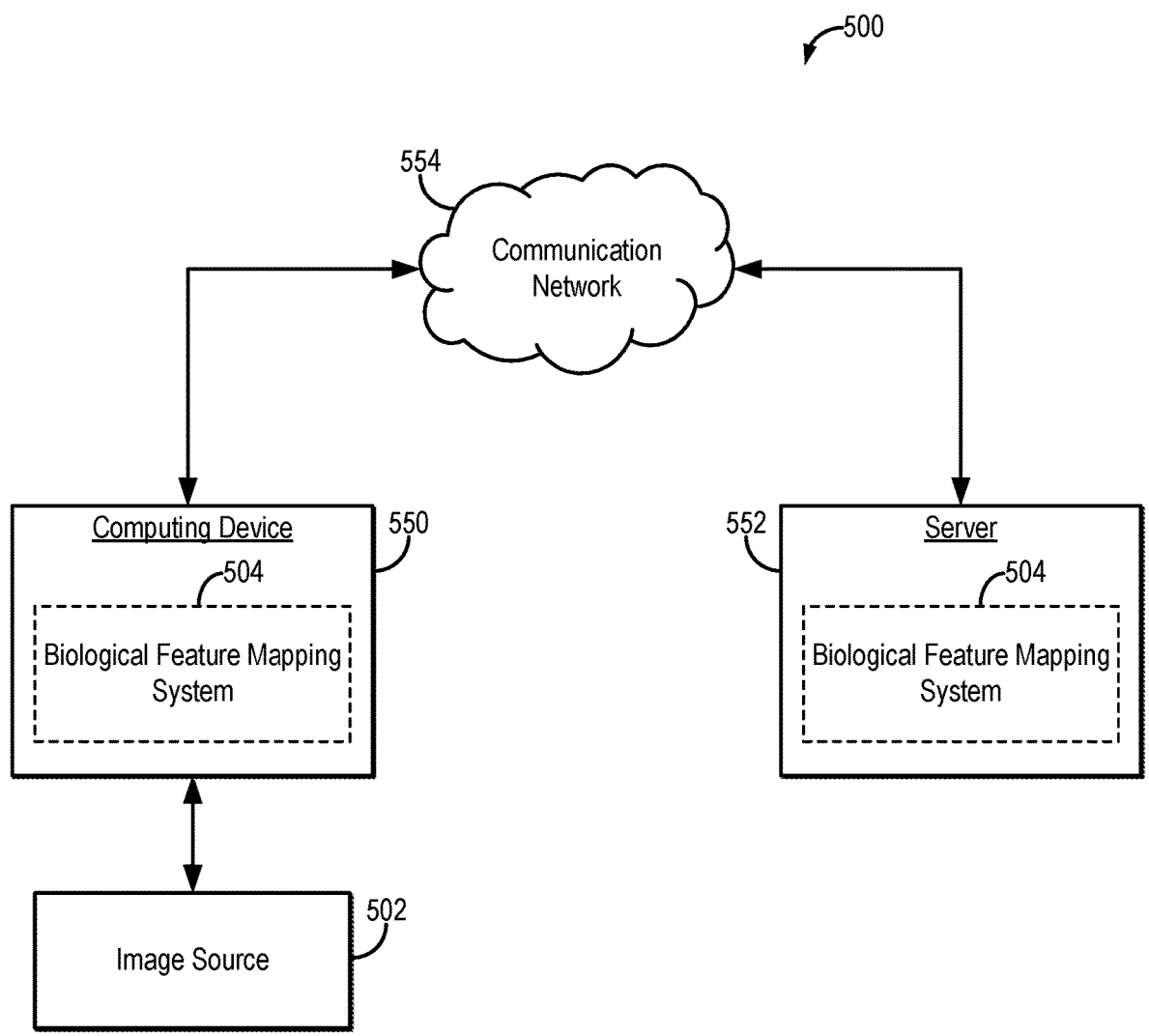
FIG. 5 is a block diagram of an example system that can implement a biological feature mapping system for generating biological feature maps or otherwise measuring or predicting biological features using a hybrid machine learning and mechanistic model.

Referring now to FIG. 5, an example of a system 500 for generating and implementing a hybrid machine learning and mechanistic model in accordance with some embodiments of the systems and methods described in the present disclosure is shown. As shown in FIG. 5, a computing device 550 can receive one or more types of data (e.g., multiparametric MRI data, image-localized biopsy data, cell density map data, biological feature data) from image source 502. In some embodiments, computing device 550 can execute at least a portion of a biological feature mapping system 504 to generate biological feature maps (e.g., cell density maps) or otherwise measure or predict biological features from data received from the image source 502.

Additionally or alternatively, in some embodiments, the computing device 550 can communicate information about data received from the image source 502 to a server 552 over a communication network 554, which can execute at least a portion of the biological feature mapping system 504 to generate biological feature maps (e.g., cell density maps) or otherwise measure or predict biological features from data received from the image source 502. In such embodiments, the server 552 can return information to the computing device 550 (and/or any other suitable computing device) indicative of an output of the biological feature mapping system 504 to generate biological feature maps (e.g., cell density maps) or otherwise measure or predict biological features from data received from the image source 502.

In some embodiments, computing device 550 and/or server 552 can be any suitable computing device or combination of devices, such as a desktop computer, a laptop computer, a smartphone, a tablet computer, a wearable computer, a server computer, a virtual machine being executed by a physical computing device, and so on. The computing device 550 and/or server 552 can also reconstruct images from the data.

In some embodiments, image source 502 can be any suitable source of image data (e.g., measurement data, images reconstructed from measurement data), such as an MRI system, another computing device (e.g., a server storing image data), and so on. In some embodiments, image source 502 can be local to computing device 550. For example, image source 502 can be incorporated with computing device 550 (e.g., computing device 550 can be configured as part of a device for capturing, scanning, and/or storing images). As another example, image source 502 can be connected to computing device 550 by a cable, a direct wireless link, and so on. Additionally or alternatively, in some embodiments, image source 502 can be located locally and/or remotely from computing device 550, and can communicate data to computing device 550 (and/or server 552) via a communication network (e.g., communication network 554).

In some embodiments, communication network 554 can be any suitable communication network or combination of communication networks. For example, communication network 554 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CD MA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 5 can each be any suitable communications link or combination of communications links, such as wired links, fiber optic links, Wi-Fi links, Bluetooth links, cellular links, and so on.

Figure 6:
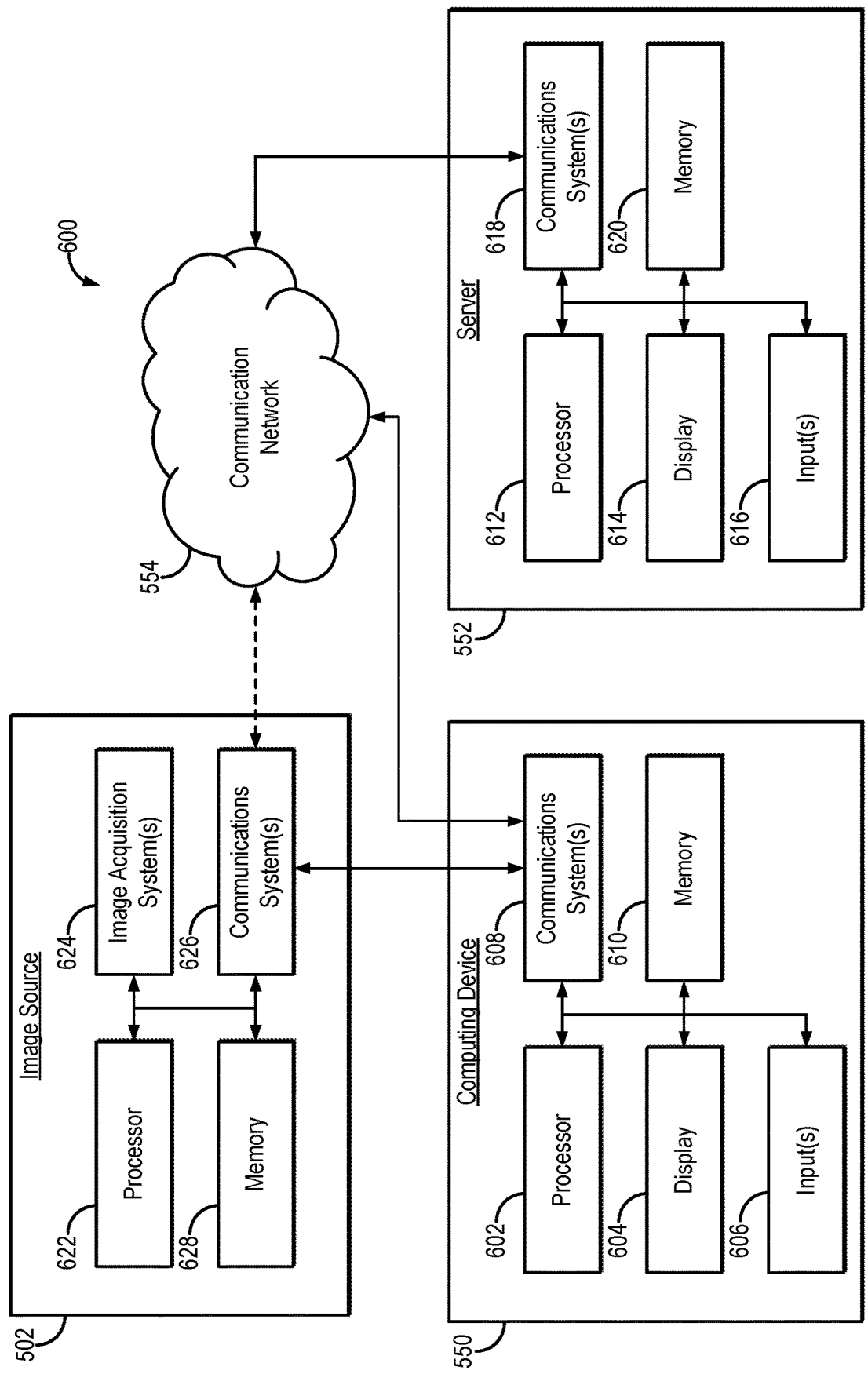
FIG. 6 is a block diagram of example hardware components of the system of FIG. 5.

Referring now to FIG. 6, an example of hardware 600 that can be used to implement image source 502, computing device 550, and server 554 in accordance with some embodiments of the systems and methods described in the present disclosure is shown. As shown in FIG. 6, in some embodiments, computing device 550 can include a processor 602, a display 604, one or more inputs 606, one or more communication systems 608, and/or memory 610. In some embodiments, processor 602 can be any suitable hardware processor or combination of processors, such as a central processing unit ("CPU"), a graphics processing unit ("GPU"), and so on. In some embodiments, display 604 can include any suitable display devices, such as a computer monitor, a touchscreen, a television, and so on. In some embodiments, inputs 606 can include any suitable input devices and/or sensors that can be used to receive user input, such as a keyboard, a mouse, a touchscreen, a microphone, and so on.

In some embodiments, communications systems 608 can include any suitable hardware, firmware, and/or software for communicating information over communication network 554 and/or any other suitable communication networks. For example, communications systems 608 can include one or more transceivers, one or more communication chips and/or chip sets, and so on. In a more particular example, communications systems 608 can include hardware, firmware and/or software that can be used to establish a Wi-Fi connection, a Bluetooth connection, a cellular connection, an Ethernet connection, and so on.

In some embodiments, memory 610 can include any suitable storage device or devices that can be used to store instructions, values, data, or the like, that can be used, for example, by processor 602 to present content using display 604, to communicate with server 552 via communications system(s) 608, and so on. Memory 610 can include any suitable volatile memory, non-volatile memory, storage, or any suitable combination thereof. For example, memory 610 can include RAM, ROM, EEPROM, one or more flash drives, one or more hard disks, one or more solid state drives, one or more optical drives, and so on. In some embodiments, memory 610 can have encoded thereon, or otherwise stored therein, a computer program for controlling operation of computing device 550. In such embodiments, processor 602 can execute at least a portion of the computer program to present content (e.g., images, user interfaces, graphics, tables), receive content from server 552, transmit information to server 552, and so on.

In some embodiments, server 552 can include a processor 612, a display 614, one or more inputs 616, one or more communications systems 618, and/or memory 620. In some embodiments, processor 612 can be any suitable hardware processor or combination of processors, such as a CPU, a GPU, and so on. In some embodiments, display 614 can include any suitable display devices, such as a computer monitor, a touchscreen, a television, and so on. In some embodiments, inputs 616 can include any suitable input devices and/or sensors that can be used to receive user input, such as a keyboard, a mouse, a touchscreen, a microphone, and so on.

In some embodiments, communications systems 618 can include any suitable hardware, firmware, and/or software for communicating information over communication network 554 and/or any other suitable communication networks. For example, communications systems 618 can include one or more transceivers, one or more communication chips and/or chip sets, and so on. In a more particular example, communications systems 618 can include hardware, firmware and/or software that can be used to establish a Wi-Fi connection, a Bluetooth connection, a cellular connection, an Ethernet connection, and so on.

In some embodiments, memory 620 can include any suitable storage device or devices that can be used to store instructions, values, data, or the like, that can be used, for example, by processor 612 to present content using display 614, to communicate with one or more computing devices 550, and so on. Memory 620 can include any suitable volatile memory, non-volatile memory, storage, or any suitable combination thereof. For example, memory 620 can include RAM, ROM, EEPROM, one or more flash drives, one or more hard disks, one or more solid state drives, one or more optical drives, and so on. In some embodiments, memory 620 can have encoded thereon a server program for controlling operation of server 552. In such embodiments, processor 612 can execute at least a portion of the server program to transmit information and/or content (e.g., data, images, a user interface) to one or more computing devices 550, receive information and/or content from one or more computing devices 550, receive instructions from one or more devices (e.g., a personal computer, a laptop computer, a tablet computer, a smartphone), and so on.

In some embodiments, image source 502 can include a processor 622, one or more image acquisition systems 624, one or more communications systems 626, and/or memory 628. In some embodiments, processor 622 can be any suitable hardware processor or combination of processors, such as a CPU, a GPU, and so on. In some embodiments, the one or more image acquisition systems 624 are generally configured to acquire data, images, or both, and can include an RF transmission and reception subsystem of an MRI system. Additionally or alternatively, in some embodiments, one or more image acquisition systems 624 can include any suitable hardware, firmware, and/or software for coupling to and/or controlling operations of an MRI system or an RF subsystem of an MRI system. In some embodiments, one or more portions of the one or more image acquisition systems 624 can be removable and/or replaceable.

Note that, although not shown, image source 502 can include any suitable inputs and/or outputs. For example, image source 502 can include input devices and/or sensors that can be used to receive user input, such as a keyboard, a mouse, a touchscreen, a microphone, a trackpad, a trackball, and so on. As another example, image source 502 can include any suitable display devices, such as a computer monitor, a touchscreen, a television, etc., one or more speakers, and so on.

In some embodiments, communications systems 626 can include any suitable hardware, firmware, and/or software for communicating information to computing device 550 (and, in some embodiments, over communication network 554 and/or any other suitable communication networks). For example, communications systems 626 can include one or more transceivers, one or more communication chips and/or chip sets, and so on. In a more particular example, communications systems 626 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 628 can include any suitable storage device or devices that can be used to store instructions, values, data, or the like, that can be used, for example, by processor 622 to control the one or more image acquisition systems 624, and/or receive data from the one or more image acquisition systems 624; to images from data; present content (e.g., images, a user interface) using a display; communicate with one or more computing devices 550; and so on. Memory 628 can include any suitable volatile memory, non-volatile memory, storage, or any suitable combination thereof. For example, memory 628 can include RAM, ROM, EEPROM, one or more flash drives, one or more hard disks, one or more solid state drives, one or more optical drives, and so on. In some embodiments, memory 628 can have encoded thereon, or otherwise stored therein, a program for controlling operation of image source 502. In such embodiments, processor 622 can execute at least a portion of the program to generate images, transmit information and/or content (e.g., data, images) to one or more computing devices 550, receive information and/or content from one or more computing devices 550, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Although the systems and methods described in the present disclosure have been described with respect to mechanistic models of biological and/or physiological processes, it will be appreciated that the hybrid machine learning and mechanistic models can be applicable to estimate feature data associated with other systems, too. In these instances, feature data can be mapped, measured, predicted, or otherwise estimated using a hybrid machine learning and mechanistic model that is suitably trained on relevant training data. Examples of other applications include atmospheric models, meteorological models, polling data models, and so on.

Generally, these more general hybrid machine learning and mechanistic models can be used to map, measure, predict, or otherwise estimate feature data that may be spatially and/or temporally resolved data. Input data can include 2D and/or 3D maps of data relevant to the underlying mechanistic model used to augment the machine learning model. Such mechanistic models may include an adaptation of the proliferation-invasion model to mathematically describe a rate of change of a density of a given population of items as a function of invasion of the item into nearby locations and increase of items.

Another example of an ecologically equivalent scenario is in predicting animal and insect repopulation of a forest that has been partially destroyed by fire and imaged by satellite. More generally, any spatial-temporal system that is traditionally viewed from a macroscopic view (e.g., biomedical or satellite imagery), but encompasses individual level behavior and population level dynamics could have feature maps generated using the systems and methods described in the present disclosure.

The present disclosure has described one or more preferred embodiments, and it should be appreciated that many equivalents, alternatives, variations, and modifications, aside from those expressly stated, are possible and within the scope of the invention.

The invention claimed is:

1. A method for constructing and implementing a hybrid machine learning and mechanistic model to predict biological feature data, the steps of the method comprising:
   constructing a hybrid machine learning and mechanistic model by:
   (i) accessing training data with a computer system, the training data including labeled data and unlabeled data;
   (ii) training a machine learning model based on the training data, generating output that includes a trained machine learning model;
   (iii) augmenting the machine learning model using a mechanistic model that mathematically describes at least one of a biological process or a physiological process associated with a biological feature, generating a hybrid model comprising a hybrid machine learning and mechanistic model; and
   generating predicted biological feature data by inputting multiparametric magnetic resonance images to the hybrid model.

2. The method as recited in claim 1, wherein the mechanistic model is a proliferation-invasion model that mathematically describes a rate of change of cell density as a function of invasion of cells into nearby tissues and proliferation of cells.

3. The method as recited in claim 1, wherein the labeled data in the training data comprises image-localized biopsy data and the unlabeled data in the training data comprises multiparametric magnetic resonance images.

4. The method as recited in claim 3, wherein the labeled data are augmented with virtual biopsy data comprising cell density data that are generated using the mechanistic model.

5. The method of claim 1, wherein the machine learning model is a semi-supervised learning (SSL) model.

6. The method of claim 5, wherein the SSL model is a graph-based SSL model, and wherein augmenting the machine learning model using the mechanistic model comprises estimating edge weights as a function of localized features in the unlabeled data and of cell density values estimated by the mechanistic model.

7. The method of claim 6, wherein the SSL model includes incorporating a Proliferation-Invasion (PI)-estimated regional cell density into a graph-based SSL using:

$$f^* = \underset{f \in \mathcal{H}_K}{\mathrm{argmin}} \frac{1}{L} \sum_{l=1}^{L} (y_l - f(x_l))^2 + \gamma_A \|f\|_K^2 + \frac{\gamma_I}{\sum_{i,j} w_{ij}} f^T \Omega f$$

wherein L is a number of biopsy samples in a training dataset, $y_l$ is a pathologically measured tumor cell density for the l-th biopsy sample, $x_l$ contains features computed from a localized region of multiparametric MRI corresponding to a biopsy location and a tumor density prediction of the mechanistic model, $f(x_l)$ is a predictive function for cell density, $(y_l - f(x_l))^2$ is a loss function that measures a discrepancy between the pathologically measured cell density and a predicted density of each biopsy sample, $f$ is a function on a reproducing kernel Hilbert space (RKHS), $\mathcal{H}_K$, with a Mercer kernel K, $\|f\|_K^2$ is a norm on $\mathcal{H}_K$, $\gamma_A$ is a tuning parameter, f contains predictive density for each labeled and unlabeled sample, $\Sigma_{i,j} w_{ij}$ is a sum of all edge weights in a graph used by the graph-based SSL.

8. The method of claim 1, wherein the multiparametric magnetic resonance images include images of T1 with contrast, T2 weighted, Echo-planar imaging (EPI) with contrast, mean diffusivity (MD), fractional anisotropy (FA), and relative cerebral blood volume (rCBV).

9. The method of claim 1, wherein the hybrid model includes tuning parameters configured to minimize a mean absolute prediction error (MAPE) of the region of interest.

10. The method of claim 9, wherein the tuning parameters include patient-specific tuning parameters trained for each subject to minimize the MAPE of the specific subject.

11. The method of claim 9, wherein the tuning parameters include uniform tuning parameters configured to minimize the MAPE across all subjects.

12. The method of claim 11, wherein the mechanistic model is a Proliferation Invasion (PI) model of the form:

$$\underbrace{\frac{\partial c}{\partial t}}_{\substack{\text{Rate of Change} \\ \text{of Cell Density}}} = \underbrace{\nabla \cdot (D(x) \nabla c)}_{\substack{\text{Invasion of Cells} \\ \text{into Nearby Tissue}}} + \underbrace{\rho c \left(1 - \frac{c}{K}\right)}_{\substack{\text{Proliferation} \\ \text{of cells}}};$$

wherein $c(x,t)$ is a tumor cell density, $D(x)$ is a net rate of diffusion, $\rho$ is a net rate of proliferation, and K is a cell carrying capacity.

* * * * *